US006602250B2

(12) United States Patent
Karpiel et al.

(10) Patent No.: US 6,602,250 B2
(45) Date of Patent: Aug. 5, 2003

(54) ECHOGENIC WIRE KNIFE

(75) Inventors: John A. Karpiel, Winston-Salem, NC (US); Donagh O'Sullivan, Tipperary (IE)

(73) Assignees: Wilson-Cook Medical Incorporated, Winston-Salem, NC (US); Cook Ireland Ltd., Limerick (IE)

( * ) Notice: Subject to any disclaimer, the term of this patent is extended or adjusted under 35 U.S.C. 154(b) by 28 days.

(21) Appl. No.: 09/774,442

(22) Filed: Jan. 31, 2001

(65) Prior Publication Data

US 2001/0047168 A1 Nov. 29, 2001

Related U.S. Application Data

(60) Provisional application No. 60/179,194, filed on Jan. 31, 2000.

(51) Int. Cl.$^7$ .............................................. A61B 18/14
(52) U.S. Cl. ........................................ 606/45; 606/49
(58) Field of Search .............................. 606/41, 45, 48, 606/49; 607/101, 102

(56) References Cited

U.S. PATENT DOCUMENTS

| | | | |
|---|---|---|---|
| 5,019,076 A | * 5/1991 | Yamanashi et al. ............ 606/45 |
| 5,230,349 A | * 7/1993 | Langberg ..................... 607/122 |
| 5,300,068 A |   4/1994 | Rosar et al. |
| 5,364,393 A | 11/1994 | Auth et al. |
| 5,515,931 A |   5/1996 | Kuckes |
| 5,536,248 A |   7/1996 | Weaver et al. |
| 5,599,300 A |   2/1997 | Weaver et al. |
| 5,800,428 A | * 9/1998 | Nelson et al. ................. 606/41 |
| 6,134,467 A | * 10/2000 | Ouchi .......................... 604/21 |
| 6,210,408 B1 | * 4/2001 | Chandrasekaran et al. ..... 606/41 |
| 6,270,495 B1 | * 8/2001 | Palermo ....................... 606/41 |
| 6,325,800 B1 | * 12/2001 | Durgin et al. ................. 606/45 |
| 6,363,937 B1 | * 4/2002 | Hovda et al. ................ 128/898 |
| 6,395,003 B1 | * 5/2002 | Ouchi .......................... 606/46 |
| 2002/0035363 A1 | * 3/2002 | Edwards et al. ............... 606/41 |

FOREIGN PATENT DOCUMENTS

| DE | 19849964 | 5/1999 |
|---|---|---|
| EP | 316995 | * 5/1989 |
| EP | 283122 | 9/1998 |
| WO | 9952459 | 10/1999 |
| WO | 0050115 | 8/2000 |

OTHER PUBLICATIONS

The Biomedical Engineering Handbook; Joseph D. Bronzino, Chapter 83; pp. 1292–1299; CRC Press.

New Methods New Materials; Robert D. Tucker, PhD, MD, and Stephen E. Silvis, MD; Gastrointestinal Endoscopy; vol. 35, No. 1, 1989; pp. 45–47.

Capacitive Coupled Stray Currents during Laparoscopic and Endoscopic Electrosurgical Procedures; Robert D. Tucker, PhD, MD, C. Randle Voyles, MD, and Stephen E. Silvis, MD; Biomedical Instrumentation & Technology; pp. 303–311; Jul.–Aug. 1992.

Skin Burns From Electrosurgical Current; J.A. Pearce, PhD. Et al.; Medical Instrumentation, vol. 17, No. 3, May–Jun., 1983.

Laparoscopic Electrosurgery Complications and Prevention; R.D. Tucker, PhD., MD.

The Effect of Guidewires During Electrosurgical Sphincterotomy; Frederick C. Johlin, MD, Robert D. Tucker, PhD, MD, and Scott Ferguson; Gastrointestinal Endoscopy; vol. 35, No. 5, 1992; pp. 536–540.

Electrosurgical Safety of Guide Wires During Endoscopic Sphincterotomy; Richard B. Sisken, MS, PE, Neal E. Fearnot, PhD, Heidi J. Smith, PhD; Gastrointestinal Endoscopy; vol. 39, No. 6, 1993; pp. 770–773.

\* cited by examiner

*Primary Examiner*—John A. Jeffery
(74) *Attorney, Agent, or Firm*—Brinks Hofer Gilson & Lione (57) ABSTRACT

A medical device for heat treatment of patient tissue includes an electrically conductive wire guide. The wire guide has a distal end and a proximal portion. A connector is disposed on the proximal portion of the wire guide for providing electrical power to the wire guide, thereby enabling the distal end of the wire guide to heat the patient tissue.

34 Claims, 5 Drawing Sheets

ECHOGENIC WIRE KNIFE

CROSS-REFERENCE TO RELATED APPLICATIONS

This application claims the benefit of U.S. Provisional Patent Application Ser. No. 60/179,194 filed Jan. 31, 2000.

TECHNICAL FIELD

Disclosed is a medical device and more particularly, a catheter-wire guide assembly that acts as both a cutting and coagulating tool.

BACKGROUND OF THE INVENTION

Electrosurgical devices are used to rapidly heat tissue. The heating of the tissue can cause a series of concerns for the patient. Heating the tissue can dry it, it can be cut, or heating tissue can cause coagulation.

Cutting occurs when a sinusoidal waveform is continuously applied through the cutting device. Coagulation occurs if the sinusoidal waveform is applied in a series of waveform packets. Depending on the surgeons requirements, the waveform can be altered to suit the purpose of the application.

Electrosurgical devices or units (ESU) can also vary in terms of electrical pathways. For example, the ESU can be operated in a monopolar mode or a bipolar mode. In the monopolar mode, the current generally flows from a relatively small active electrode into the situs, through the body, and returns via a large dispersive electrode. The dispersive electrode can be placed above or below the patient as required. Therefore, in monopolar mode, the current density at the situs is high, causing heat transfer at the situs thereby achieving cutting or coagulation. On the other hand, the current density at the dispersive electrode is relatively low, thereby causing very little heat build-up at the dispersive electrode locale and concomitantly, less or no tissue damage. Fulguration occurs when the active electrode is not in contact with the tissue and sparks fly from the electrode to the tissue. The sparks land on different places on the tissue. Generally to achieve fulguration, a surgeon may select an interrupted current to use, in combination with high voltage (e.g. in the kilovolt range) to break down the air dielectric.

A bipolar ESU has two electrodes between which the current passes. Generally, tissue is placed between the electrodes and current travels between the electrodes and thereby through the tissue. In some embodiments, a traditional bipolar ESU is energized forceps, in which the electrodes are small and cause high current density between the forceps prongs. Therefore, generally there is no large dispersive electrode under the patient used as the passive electrode in current conduction. A large dispersive electrode, if used, is generally to provide an alternate current pathway for safety reasons. In either bipolar or monopolar mode, the current usually jumps via an arc from one electrode to either the other electrode or into the tissue itself.

Therefore, selection of the proper ESU and the proper power will lead to the desired effect. The desired effect is generally a function of the temperature of the heat applied at the situs. For example, body tissue that heats to 45° C. can still be cooled back to normal without concomitant tissue damage. However, when the temperature is greater than 45° C., then irreversible tissue damage occurs. Between 45° C. and 60° C., protein damage occurs as proteins lose their quarternary structure and may solidify into a glutinous compound. This process is known as coagulation. Between 60° C. and 100° C., the tissue dries wherein the aqueous cell contents evaporate in a process known as dessication. Above 100° C., the solid contents are reduced to carbon in a process known as carbonization. Therefore, tissue damage is a function not only of temperature, but of duration of exposure to the heat.

Problems associated with ESU surgery include active electrode burns, dispersive electrode burns, explosions of combustible materials, power line shock, muscle stimulation, nerve stimulation, or hidden alternate current pathways. The problems with burns is generally described in Pearce, Geddes, Van Vleet, Foster, and Allen, *Skin Burns From Electrosurgical Current*, Vol. 17(3), Medical Instrumentation, pg. 226 (May 1983), the disclosure of which is expressly incorporated by reference.

Other problems with ESU surgery include manipulation problems. For example, since the traditional ESU involves many instruments, wires, power sources, etc., there is an increased tendency that wires are crossed, many devices are necessary all of which, which cause overall confusion during the procedure. That many devices are needed, including electrical devices, the incidence of electromagnetic interference with other devices is increased. Since the ultimate result of the electrosurgery often is access to the vascular system, then catheterization procedures are needed. Such procedures also entail many devices such as catheters, wire guides, sheaths, and the like. Therefore, when combining the electrosurgery with catheterization, the number of devices increases dramatically.

SUMMARY OF THE INVENTION

The foregoing problems and a technical advance is achieved in the present invention. Disclosed a is medical device in which the wire guide also serves as an ESU.

DETAILED DESCRIPTION

Figure 1:
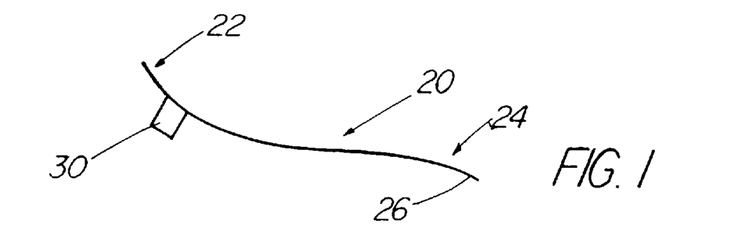
FIG. 1 is a schematic view of an embodiment of a medical device according to the present invention.

FIG. 1 demonstrates a simple embodiment of the present invention. A wire guide 20 (sometimes referred to as a guidewire) is shown having a wire guide proximal portion 22 and a wire guide distal end 24. The wire guide 20 also has a wire guide tip 26, located at the distal end. The wire guide tip 26 is the end that will enter the patient first and/or form the cutting edge. Somewhere along the proximal portion 22 is a connector 30. The connector 30 is used to connect a power supply to the wire guide. Intuitively therefore, the wire guide 20 should comprise a material capable of conducting power or current. The wire guide 20 can take many configurations such as, but not limited to, a helical wire guide, a simple wire, a braided wire, or the like. The wire guide 20 can be, for example, a THSF 0.035"–480 cm wire guide or preferably a TMT 0.035"–480 cm wire guide, each available from Wilson-Cook, Inc. of Winston-Salem, N.C. These are TEFLON® coated wire guide of the 300 series stainless steel helical coiled wire with a safety wire, the latter having a movable core, allowing the user to change the distal end 24 from stiff to floppy after the electrosurgical heat treatment (e.g., cutting, puncturing) has been completed. It is contemplated that the stiff end will be the cutting edge of the wire guide knife. To provide greater control of the distal end cutting edge 26, the wire guide can be so fabricated as to have a stiffer or higher durometer material at the cutting edge. It should be recognized, however, that the wire guide 20 can be of any diameter, width, or length for its intended use.

Figure 2:
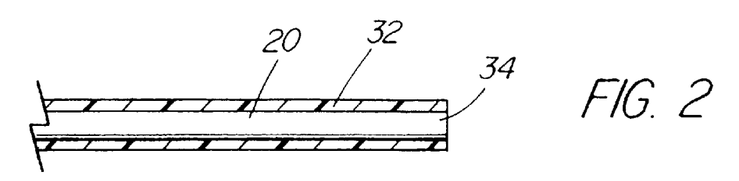
FIG. 2 is a cross-sectional view of a first embodiment of a distal portion of a wire guide constructed in accordance with the present invention.

FIG. 2 demonstrates another embodiment of the invention. Because the wire guide 20 will be carrying current or power of some type, another embodiment of the present invention involves using an insulating layer 32 disposed over the wire guide 20. The insulating layer can be TEFLON® (polytetrafluoroethylene) or any other type of insulating material. The insulating layer 32 can be selected depending on the degree of insulation required, such as those complying with Standards IEC 60601-2-2, IEC 601-2-18, and AAMI HF 18. The purpose of the insulating layer is to minimize or extinguish the risk of electrocution or other electrical hazards posed to the surgeon or patient. Accordingly, the insulating layer is intended to include known insulating materials. One such material is disclosed in U.S. Pat. No. 5,197,468 to Proctor et al., the disclosure of which is expressly incorporated by reference.

Figure 3:
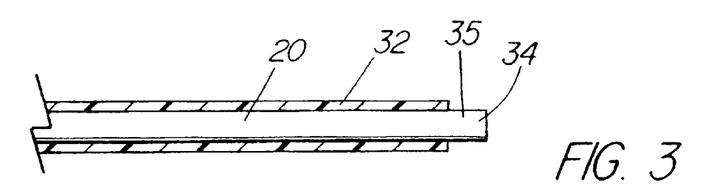
FIG. 3 is a cross-sectional view of a second embodiment of a distal portion of a wire guide constructed in accordance with the present invention.

With reference to FIGS. 2 and 3, shown is another embodiment of the present invention. In FIG. 2, the insulating layer 32 terminates coincident with a wire guide blunt end 34. In FIG. 3 however, the insulating layer 32 terminates somewhat proximal to the blunt end 34. In fabrication of the device, the insulating layer 32 can be made such that it terminates proximal to the blunt end 34, or can be made where the insulating layer 32 covering the blunt end 34 is subsequently removed or scraped off to expose an uninsulated end 35.

Figure 4:
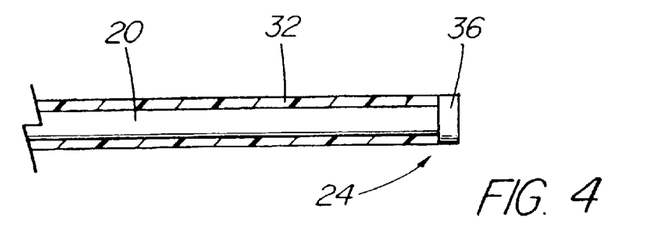
FIG. 4 is a cross-sectional view of a third embodiment of a distal portion of a wire guide constructed in accordance with the present invention.

With reference to FIG. 4, shown is another embodiment of the present invention in which the wire guide distal end 24 is provided with a conductive tip 36. The conductive tip 36 can be so designed to maximize electrical conductivity, or to alter the current density at the situs. For example, the conductive tip 36 can be rounded, invaginated, or blunt ended. The desired shape may alter the arc pattern from more of a fulguration pattern to a single arc.

Figure 5:
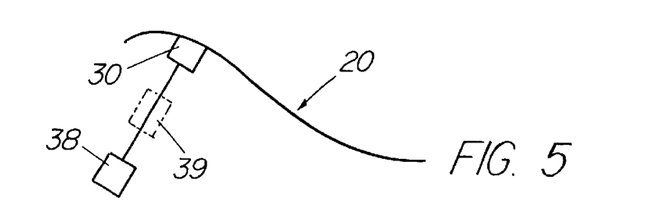
FIG. 5 is a schematic view of an embodiment of the energization of a wire guide in accordance with the present invention.

FIG. 5 begins a more complex embodiment of the invention. Shown is the wire guide 20 connected to a connector 30. Since one purpose of the invention is to energize the wire guide 20, a power supply or power source 38 is needed. Power source 38 is shown being directly attached to the connector. As shown in dotted lines, there may be one or more intermediate connectors 39 generally between the connector 30 and the power source 38. The intermediate connector may perform several functions such as voltage regulation, power regulation, monitoring, or provide several other useful indicia.

The power source 38 should be selected depending on the intended use of the device. A power source can generate RF signals. The electrical supply can be monopolar. As the device may differ from country to country, the supply can be of varying voltage, such as 220 V. A suggested frequency is about 50 Hz having a power of about 400 W. A suggested current could range from 0.01 amps to 2.0 amps but suggestibly is between 1.1 and 1.82 amps. The following tables illustrate suggested or exemplary parameters for the ESU.

TABLE 1

Power Settings For Desired Surgical Procedures

A. Low Power (<30 W for cutting or coagulation)
neurosurgery, dermatology, plastic surgery, oral surgery, laparoscopic sterilization, vasectomy
B. Medium Power (30–150 W for cutting; 30–70 W for coagulation)
general surgery, laparatomies, head/neck surgery, orthopaedic surgery, vascular surgery, thoracic surgery, polypectomy
C. High Power (>150 W for cutting; >70 W for coagulation)
transurethral resection procedures, thoracotomies, ablative cancer surgery, mastectomies

TABLE 2

Impedance (Ohms) Ranges Monitored During Surgery

Prostrate tissue (400–700 Ω); Oral Cavity (1000–2000 Ω); Gall Bladder (1500–2400 Ω); Skin (1700–2500 Ω); Bowel (2500–3000 Ω); Mesentery (3000–4200 Ω); Adipose (3500–4500 Ω)

TABLE 3

Some Output Characteristics of ESU's

| Mode | Output Voltage Range Open Circuit, Vpeak -peak | Output Power Range, W | Freq. kHz | Crest Factor |
|---|---|---|---|---|
| Cut (MP) | 200–5000 | 1–400 | 300–1750 | 1.4–2.1 |
| Blend (MP) | 1500–5800 | 1–300 | 300–1750 | 2.1–6.0 |
| Dessicate (MP) | 400–6500 | 1–200 | 300–800 | 3.5–6.0 |
| Fulgurate (MP) | 6000–12000 | 1–200 | 300–800 | 6.0–20.0 |
| Coag./Dess. (BP) | 400–100 | 1–70 | 300–1050 | 1.6–12.0 | wherein, MP means in monopolar mode and BP means in bipolar mode.

Figure 6A:
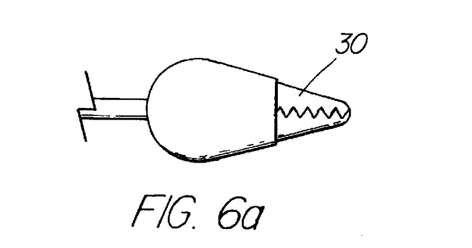
FIG. 6A is a front elevational view of an embodiment of a connector configured for use in the medical device of the present invention.
Figure 6B:
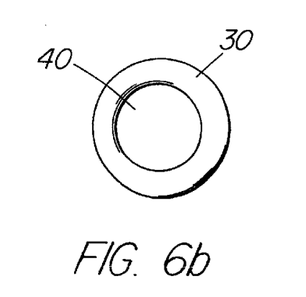
FIG. 6B is a front elevational view of another embodiment of a connector configured for use in the medical device of the present invention.
Figure 6C:
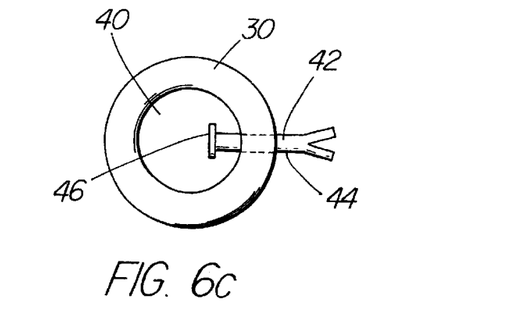
FIG. 6C is a front elevational view of further embodiment of a connector configured for use in the medical device of the present invention.
Figure 6D:
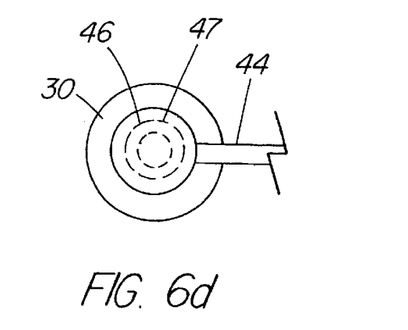
FIG. 6D is a schematic view of an additional embodiment of a connector configured for use in the medical device of the present invention.
Figure 7:
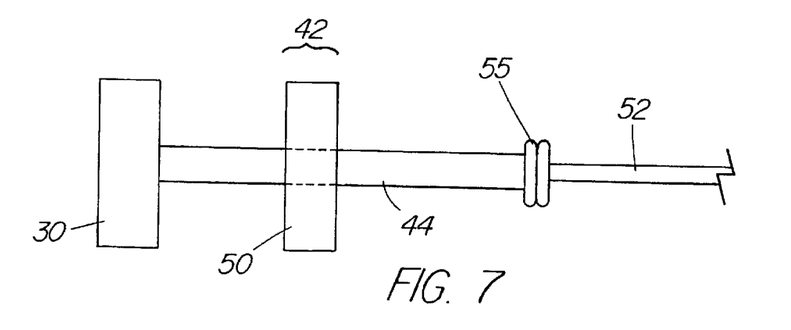
FIG. 7 is a schematic view including a still further embodiment of a connector configured for use in the medical device of the present invention.

FIGS. 6A–7 demonstrate various connectors 30. For example in FIG. 6A, shown is a connector 30 that resembles an alligator mouth and is often called an alligator clip. The connector 30 may opened and the wire guide connected to the connector 30 through the "mouth" of the connector 30. FIG. 6B demonstrates another type of connector 30 that is generally ring shaped on the interior connector lumen 40. Connector 30 can be so configured as to have a static connector lumen 40 diameter, or have a variable connector lumen 40 diameter. It is preferable to have a variable size lumen 40 since a smaller lumen will generally lead advantageously to a tighter contact between the wire guide running through the lumen and the connector 30.

FIG. 6C demonstrates another embodiment of the connector 30 of FIG. 6B. Shown again is the connector lumen 40. Intruding into the lumen 40 is a contact 42, which in one exemplary configuration is a female receptacle. The contact 42 has a contact elongated portion 44 which is sufficient length and material to facilitate the connection. The contact elongated portion 44 may also include a contact point 46, partially located in the lumen 40. As the wire guide passes through the lumen 40, the contact point 46 will engage the wire guide and provide electrical communication. The elongated portion 44 can be moveable to move the portion 44 into the lumen 40 more or out. FIG. 6D demonstrates another embodiment of the connector 30. Here, shown is a variable lumen diameter 47 connector. The lumen 40 can decrease in size by having the lumen perimeter decrease. Thus contact point 46 is not a discrete point but comprises the entire perimeter so that there is electrical connection around the wire guide and the connector. This is analogous to squeezing an extended thumb (wire guide) with the fingers (the connector).

FIG. 7 demonstrates another embodiment of the connector. Connector 30 is shown having an elongated portion 44 extending from the connector 30 into and through a contact 42 and into an intermediate connector 50. This intermediate connector 50 may be the intermediate connector 39 as discussed with reference to FIG. 5 or another intermediate connector. It can perform the same functions as described herein. The elongated portion 44 makes contact with power source wire 52 at a junction 55. Thereby, junction 55 can be separated permitting termination of the electrical communication. Furthermore, once the junction 55 separation occurs, the device is generally not connected to the power source 38 (shown schematically in FIG. 5) anymore.

Figure 8:
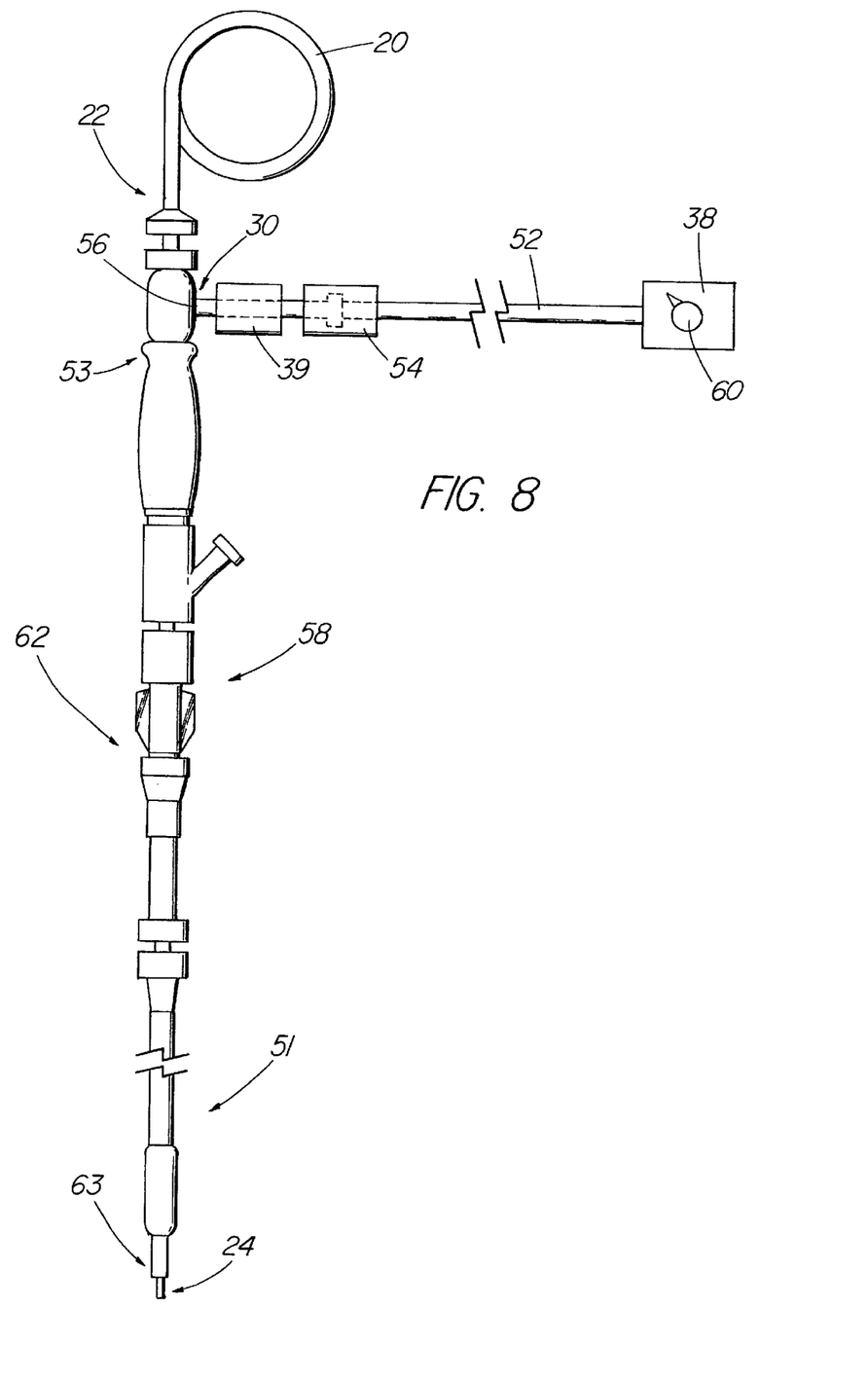
FIG. 8 is a front elevational view of a medical device constructed according to the present.

FIG. 8 demonstrates another embodiment of the invention. Shown is the catheter assembly 62 in which the wire guide 20 will partially reside. The wire guide proximal portion 22 is shown near the catheter proximal portion 53. The wire guide 20 passes through the catheter 62 and engages the connector contact 56 or connector contact point 46 (such as described with reference to FIGS. 6c and 6d). A series of intermediate connectors 39, 54 are shown providing connection with the power source 38 via the power source wire 52. The power source also can have one or more power source selectors 60 that permit selection of current applied, power source origination, voltage regulation, etc. The wire guide travels down the catheter, and perhaps through a series of catheter parts 58, which may include a series of connectors, insulators, tubings, valves, locks, etc.

Eventually, the wire guide will enter the catheter distal portion 51, a catheter distal tip 63, and exit the catheter. As shown, the wire guide distal end 24 protrudes out of the catheter. The length of the wire guide distal end 24 that protrudes is a function of the desire of the surgeon. By controlling the length of the distal end 24 protrusion, a larger cutting edge is created. One method of controlling the length of the protrusion is to control the connector 30. When the connector 30 is not completely engaging the wire guide 20, to fix the wire guide against axial movement relative to the connector 30, it is possible to enable the wire guide to move through the connector 30 and extend more or less from the catheter distal portion 51 or tip 63. One skilled in the art will recognize that a connector could be provided which would enable such axial movement of the wire guide while maintaining electrical contact between the connector and wire guide.

Figure 9:
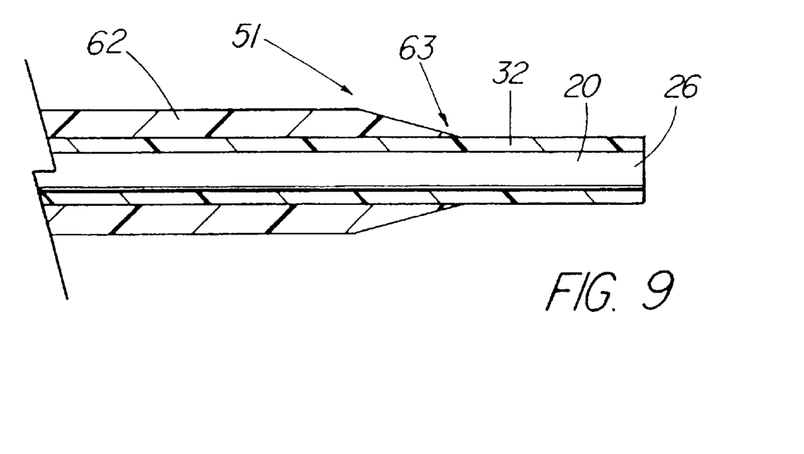
FIG. 9 is a cross-sectional view of an embodiment of a distal portion of a catheter and wire guide configured according to the present invention.

FIG. 9 demonstrates one exemplary embodiment of the catheter distal portion 51. The catheter has a catheter distal tip 63, which in this embodiment is shown as a beveled edge. Protruding from the distal tip 63 is the wire guide 20. In this embodiment, the wire guide 20 has one insulating layer 32 disposed thereover. As will be seen later, there may be a plurality of insulating layers. In this embodiment, the wire guide 20 has a wire guide tip 26, which is shown as a blunt end. As seen above, with particular reference to FIG. 4, the wire guide tip 26 may also have a metallic tip 36 (not shown in FIG. 9) such as described with reference to FIG. 4.

Figure 10:
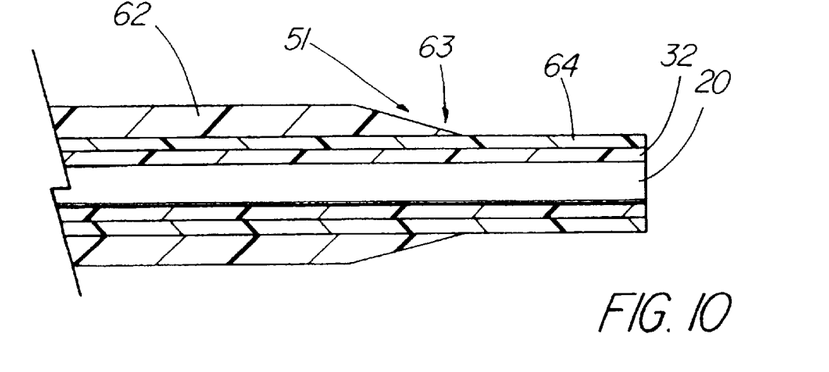
FIG. 10 is a cross-sectional view of an embodiment of a distal portion of a catheter and wire guide configured according to the present invention.
Figure 11:
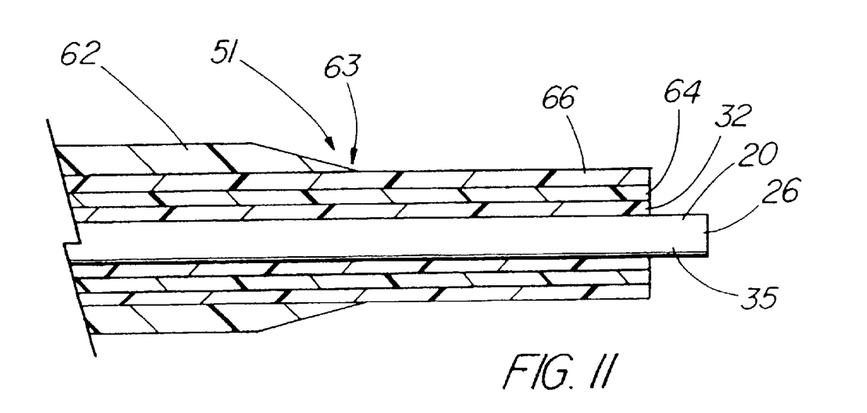
FIG. 11 is a cross-sectional view of an embodiment of a distal portion of a catheter and wire guide configured according to the present invention.

FIGS. 10 & 11 show other embodiments of the catheter distal portion 51. In FIG. 10, shown is a plurality of insulating layers, such as insulating layer 32 and a second insulating layer 64. Of course it must be remembered that in any embodiment of the present invention, the catheter body itself may also serve as an insulating layer. In this regard, the catheter 1 itself can be another insulating layer disposed over layer 64. FIG. 11 shows basically the same configuration of FIG. 10, except a third insulating layer 66 is shown.

In addition, FIG. 11 shows that the wire guide 20 is not insulated at the extreme distal portion of the wire guide tip 26 forming the uninsulated end 35. The tip of the wire may protrude from the catheter and terminate at a distance from the end of the catheter, such as 10 mm, 25 mm, or 50 mm. Therefore, as mentioned above, the catheter body may also provide a layer of insulation and thus FIG. 11 actually has at least 3 layers of insulation which may be of the same or different materials.

Figure 12:
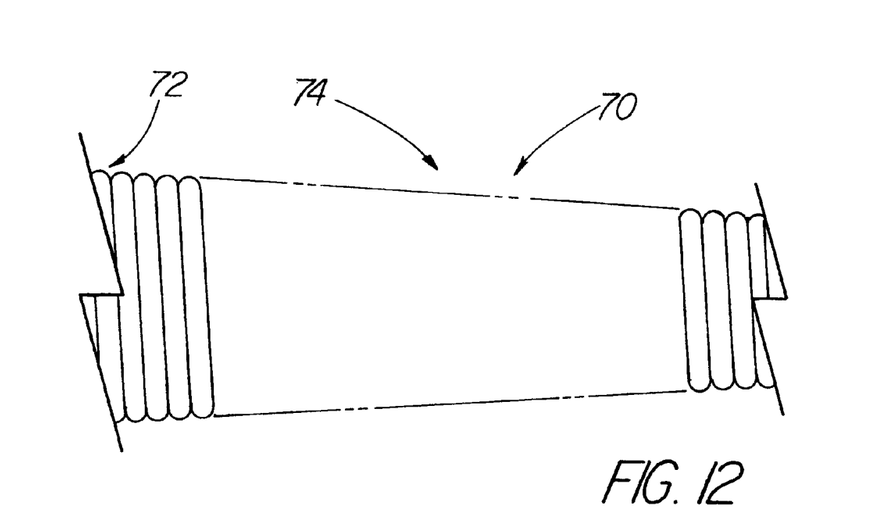
FIG. 12 is a schematic view illustrating a configuration of the wire guide of the present invention.

FIG. 12 demonstrates one configuration of the wire guide 20. The wire guide may have a tapered distal end 70. The wire guide tapers from the wire guide proximal portion 72 to the tapered distal end 70. One configuration for doing so is to make the wire guide 20 a helical wire guide 74.

Figure 13:
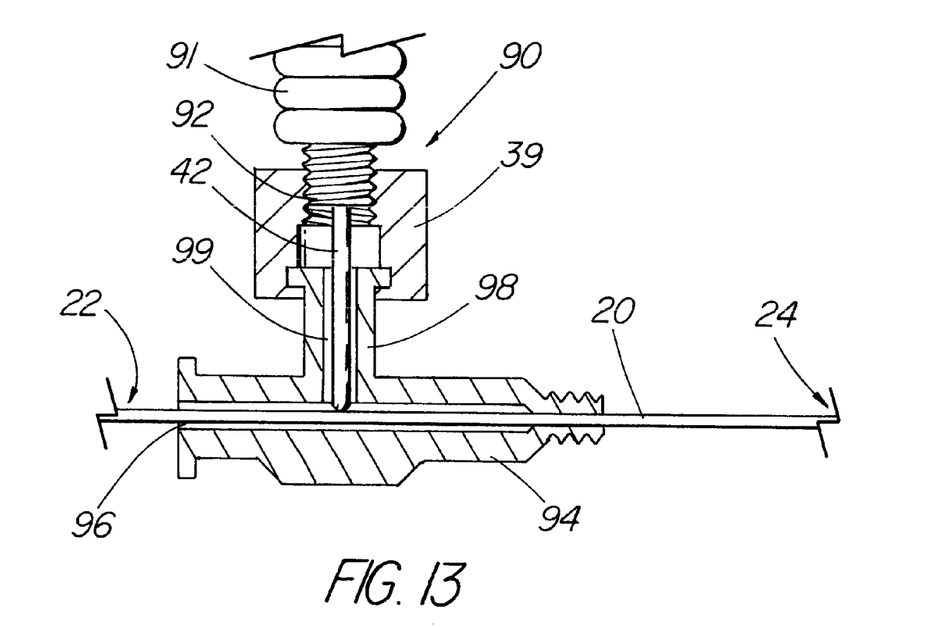
FIG. 13 demonstrates a cross sectional view of a connector assembly constructed according to the present invention.

FIG. 13 demonstrates a cross sectional view of one embodiment of a connector assembly 90. Connector assembly 90 includes an adaptor 91 that has a screw thread 92 disposed on it. Extending through the adaptor is the contact 42 which engages the wire guide 20. Connected to the adaptor 90 is an intermediate connector 39 such as a male luer lock adaptor. Connected thereto is a fitting 94, which has a fitting lumen 96 in which the wire guide 20 passes. The fitting 94 is a T-shaped fitting in which the fitting 94 has a fitting branch 98. The fitting branch 98 has a lumen 99 extending therethrough in which the contact 42 passes.

Accordingly, as the adaptor 91 is advanced by tightening the threads 92 so that the contact 42 is pressed up against the wire guide 20 in the fitting lumen 96. Electrical communication is thereby achieved as the wire guide becomes "sandwiched" between the fitting 94 and the contact 42. To protect the operators, each adaptor or connector can be insulated to minimize the chance of electrocution or burns. Any connector or adaptor having a lumen can also be lined with a insulating layer (not shown) to further protect against undesired electrical communication.

The illustrated embodiments shown herein have been set forth only for the purposes of clarity and example, and in no way should be taken as limiting the invention as defined by the appended claims, which include all equivalents whether now known or later discovered. The invention includes both embodiments comprising and consisting of the examples described.

What is claimed is:

1. A medical device for heat treatment of patient tissue, the medical device comprising:
    an electrically conductive wire guide, the wire guide having a movable core, a distal end and a proximal portion; and
    a removable connector disposed on the proximal portion of the wire guide for providing electrical power to the wire guide, thereby enabling the distal end of the wire guide to heat the patient tissue,
    wherein the medical device is configured for stiffness for use as an electro-surgical unit, and is configured for flexibility for use as a wire guide.

2. The medical device of claim 1, wherein the wire guide further comprises an insulating layer substantially covering the wire guide.

3. The medical device of claim 2, wherein the insulating layer terminates coincident with the distal end.

4. The medical device of claim 2, wherein the insulating layer comprises a biocompatible material.

5. The medical device of claim 2, wherein the insulating layer comprises polytetrafluoroethylene.

6. The medical device of claim 1, wherein the distal end further comprises a blunt end.

7. The medical device of claim 1, wherein the distal end further comprises a material of greater stiffness than material comprising the proximal portion.

8. The medical device of claim 7, wherein the distal end further comprises an insulating layer substantially covering the distal end.

9. The medical device of claim 8, wherein the insulating material further comprises polytetrafluoroethylene.

10. The medical device of claim 1, wherein the distal end comprises a metallic tip.

11. The medical device of claim 10, wherein the metallic tip further comprises a blunt end.

12. The medical device of claim 1, wherein a power source is disconnectably connected to the wire guide.

13. The medical device of claim 12, wherein the power source is disconnectably connected to a proximal portion of the wire guide.

14. The medical device of claim 12, wherein an intermediate connector is disconnectably connected to the power source.

15. The medical device of claim 12, wherein an intermediate connector is disconnectably connected to the wire guide.

16. The medical device of claim 12, wherein the power source further comprises a RF power source.

17. The medical device of claim 12, wherein the power generated is between 0 to 400 W.

18. The medical device of claim 12, wherein the power generated is between 0 to 250 W.

19. The medical device of claim 12, wherein the power generated is between 0 to 200 W.

20. The medical device of claim 12, wherein the power generated is about 200 W.

21. The medical device of claim 1, wherein the medical device is configured for stiffness or for flexibility by adjusting the movable core.

22. The medical device of claim 1, wherein the wire guide further comprises an insulating layer sufficient to substantially insulate the wire guide when power of about 400 W is passed therethrough.

23. A medical device suitable for minimally-invasive medical procedures, comprising:
    a) a wire guide having a movable core and a proximal and a distal portion, the distal portion configured for stiffness for use as an electro-surgical unit and configured for flexibility for use as a wire guide;
    b) a connector, the connector disconnectably connected to the proximal portion of the wire guide; and
    c) a power source disconnectably connected to the connector, wherein the medical device is configured for use as an electro-surgical unit when the connector is present and as a wire guide when the connector is removed.

24. The medical device of claim 23, wherein the distal portion of the wire guide further comprises an energized and a de-energized state.

25. The medical device of claim 24, wherein the power source further comprises a means for generating power to create the energized state.

26. The medical device of claim 24, wherein the wire guide further defines an electrical path from the power source to the distal portion.

27. The medical device of claim 26, wherein the electrical path further defines an energized state at the distal portion.

28. A catheter suitable for minimally invasive medical procedures, the catheter having a distal tip and a proximal portion, comprising:

(a) a wire guide having a movable core and a proximal and a distal portion, the distal portion configured for stiffness for use as an electro-surgical unit and configured for flexibility for use as a wire guide;

(b) a connector, the connector disconnectably connected to the proximal portion of the wire guide;

(c) a power source disconnectably connected to the connector; and (d) wherein the distal portion of the wire guide terminates within 50 mm of the catheter distal tip, and wherein the catheter is configured for use as an electrosurgical unit when the connector and power source are connected to the wire guide, and is configured for use as a wire guide when the connector and power source are disconnected from the catheter.

29. The catheter of claim 28, wherein the wire guide terminates within 25 mm of the catheter distal tip.

30. The catheter of claim 28, wherein the catheter is configured for stiffness or flexibility by adjusting the movable core.

31. The catheter of claim 28, wherein the wire guide terminates about the catheter distal tip.

32. The catheter of claim 28, wherein the catheter further comprises at least one lumen extending therethrough.

33. The catheter of claim 32, wherein the lumen further includes an insulating layer.

34. The catheter of claim 30, wherein the catheter further includes an insulating layer sufficient to substantially insulate the wire guide when power of about 400 W is passed therethrough.

* * * * *